(12) United States Patent
Crozier et al.

(10) Patent No.: US 11,622,807 B2
(45) Date of Patent: Apr. 11, 2023

(54) ESOPHAGEAL ABLATION TECHNOLOGY

(71) Applicant: Symple Surgical, Inc., Flagstaff, AZ (US)

(72) Inventors: Seth Crozier, Flagstaff, AZ (US); Sohail Desai, Sacramento, CA (US); Dan Kasprzyk, Flagstaff, AZ (US); Bryce Alexander Igo, Flagstaff, AZ (US)

(73) Assignee: Symple Surgical, Inc., Flagstaff, AZ (US)

( * ) Notice: Subject to any disclaimer, the term of this patent is extended or adjusted under 35 U.S.C. 154(b) by 1014 days.

(21) Appl. No.: 16/178,248

(22) Filed: Nov. 1, 2018

(65) Prior Publication Data

US 2019/0192224 A1    Jun. 27, 2019

Related U.S. Application Data

(63) Continuation-in-part of application No. 15/486,078, filed on Apr. 12, 2017, now abandoned.

(51) Int. Cl.
*A61B 18/18* (2006.01)
*A61B 18/00* (2006.01)

(52) U.S. Cl.
CPC .. *A61B 18/1815* (2013.01); *A61B 2018/0022* (2013.01); *A61B 2018/0091* (2013.01); *A61B 2018/00196* (2013.01); *A61B 2018/00208* (2013.01); *A61B 2018/00255* (2013.01); *A61B 2018/00327* (2013.01); *A61B 2018/00488* (2013.01); *A61B 2018/00577* (2013.01); *A61B 2018/00791* (2013.01); *A61B 2018/1823* (2013.01); *A61B 2018/1838* (2013.01); *A61B 2018/1846* (2013.01); *A61B 2018/1861* (2013.01)

(58) Field of Classification Search
CPC ........ A61B 18/1815; A61B 2018/0022; A61B 2018/00255; A61B 2018/00577; A61B 2018/1823; A61B 2018/1383; A61B 2018/1846; A61B 2018/1861; A61B 2018/1876
See application file for complete search history.

(56) References Cited

U.S. PATENT DOCUMENTS 5,496,311 A *  3/1996  Abele ................. A61B 18/082
                                                       606/28
2017/0189108 A1*  7/2017  Melsky ............... A61B 18/082

* cited by examiner

*Primary Examiner* — Michael F Peffley
*Assistant Examiner* — Samantha M Good
(74) *Attorney, Agent, or Firm* — Skinner and Associates; Joel Skinner

(57) ABSTRACT

An esophageal ablation system including a positioner, an elongated, flexible shaft extending from the positioner, and a microwave emitter, assembly disposed near the distal end of the shaft. The emitter assembly includes one or more microwave antennas and a balloon for spacing the antennas relative to target tissue. The device may have an inner balloon for deploying the antenna. The systems, devices and methods disclosed are useful for treating Barrett's Esophagus, Esophageal Adenocarcinoma, and Squamous Cell Carcinoma.

6 Claims, 22 Drawing Sheets

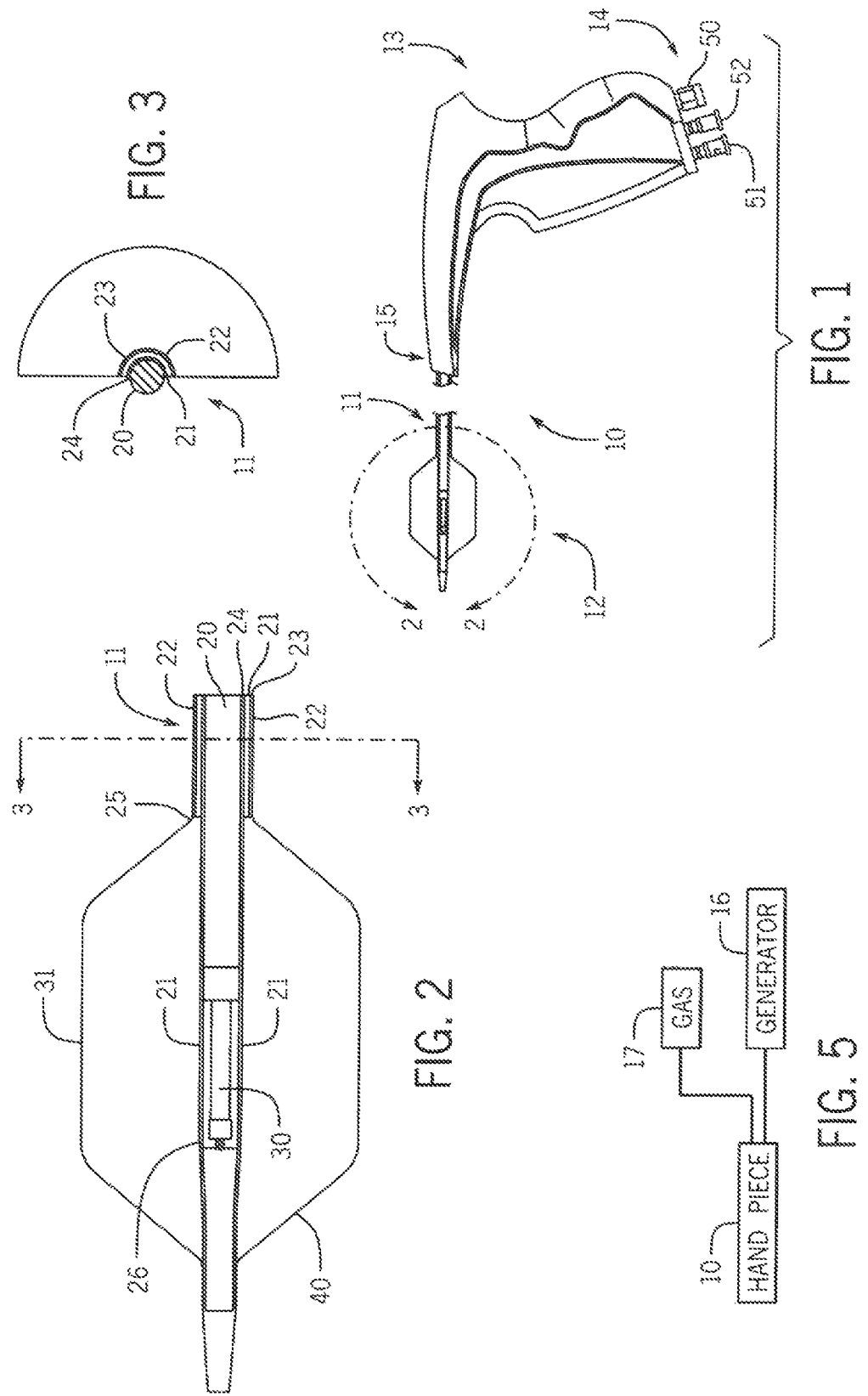

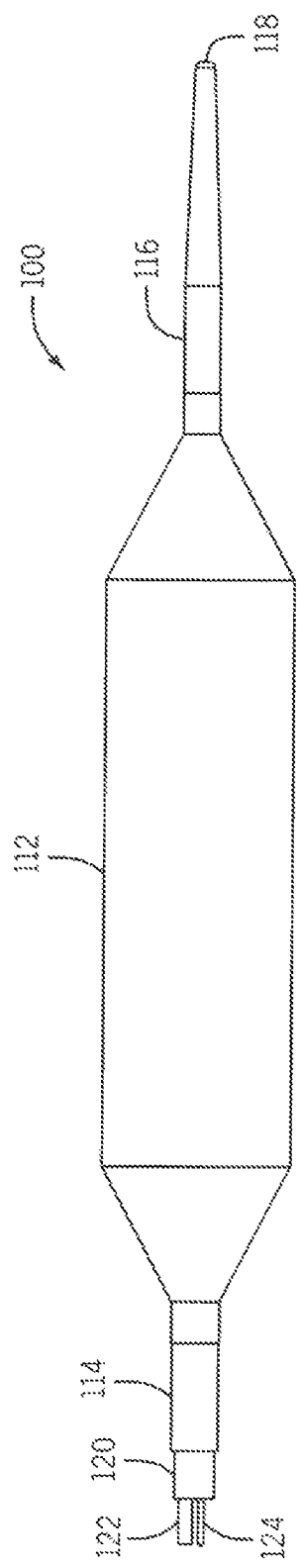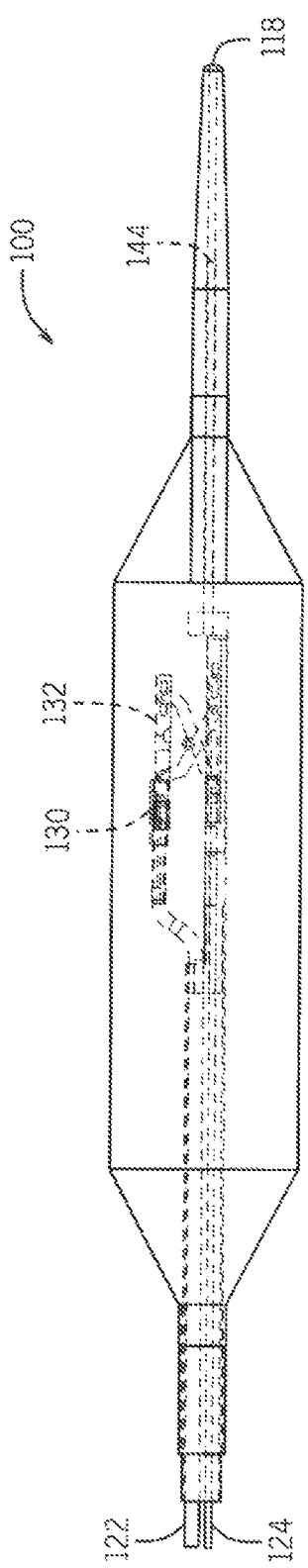
FIG. 11
FIG. 12

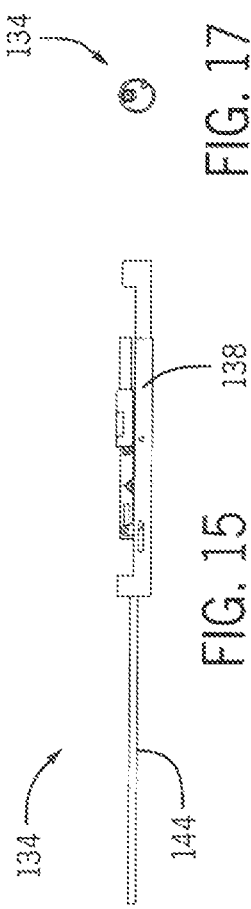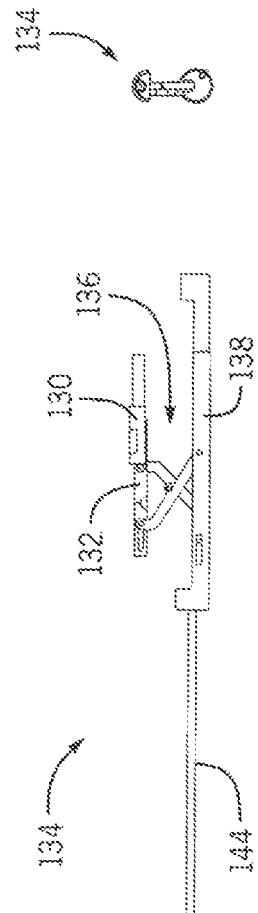

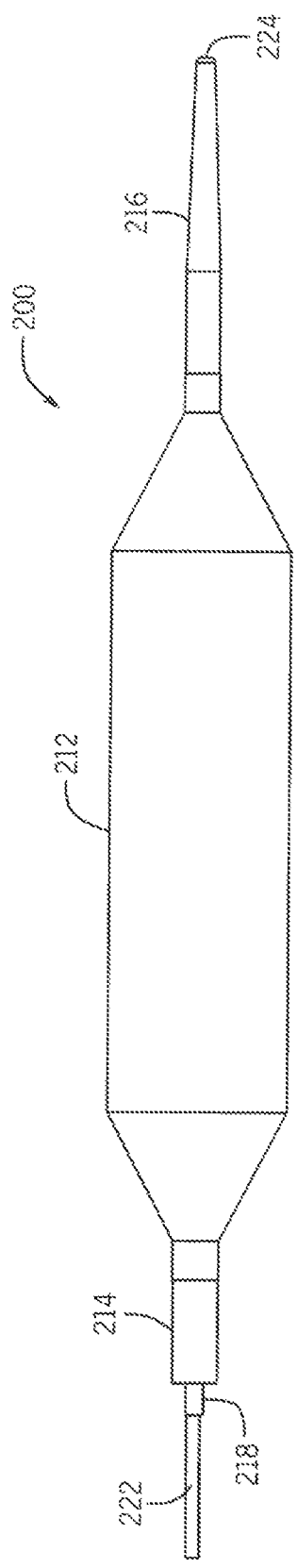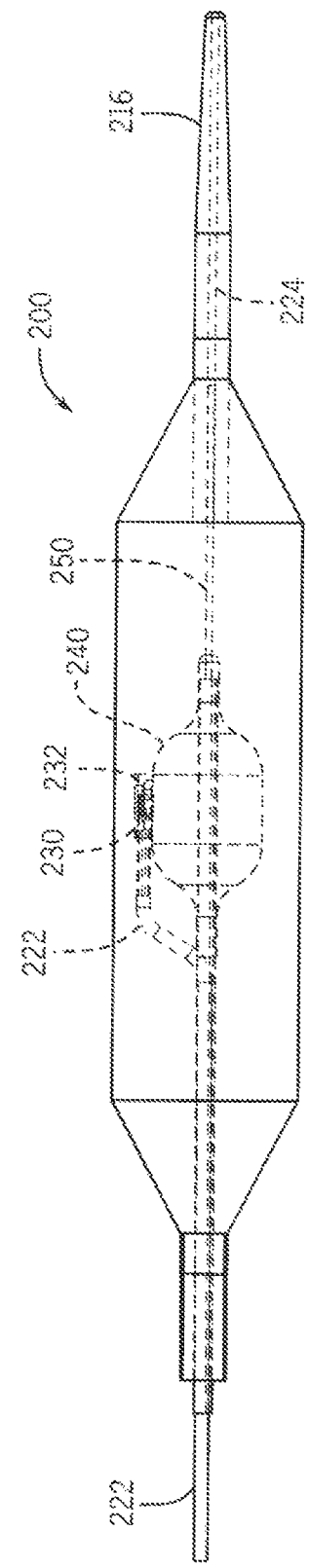
FIG. 21
FIG. 22

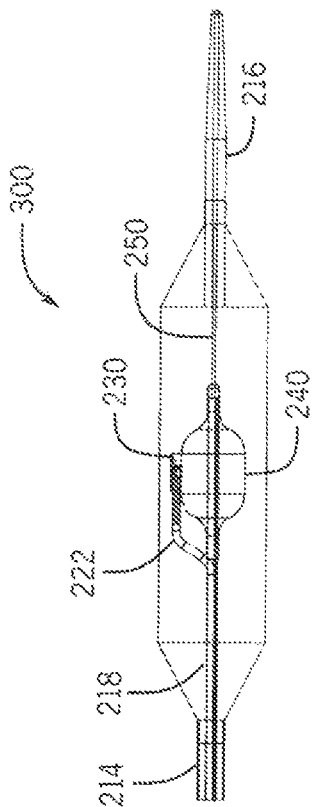
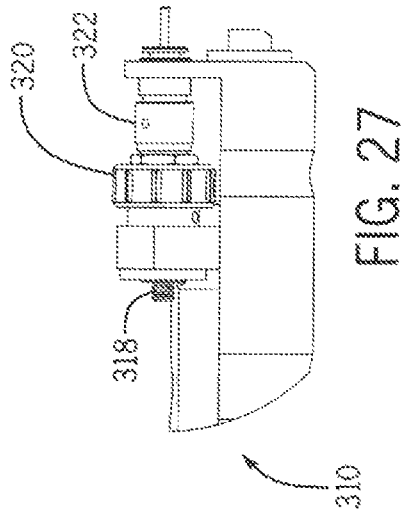
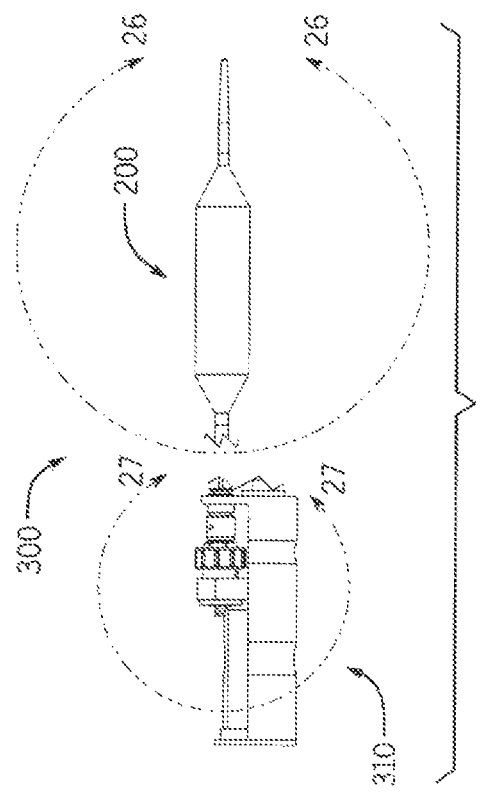
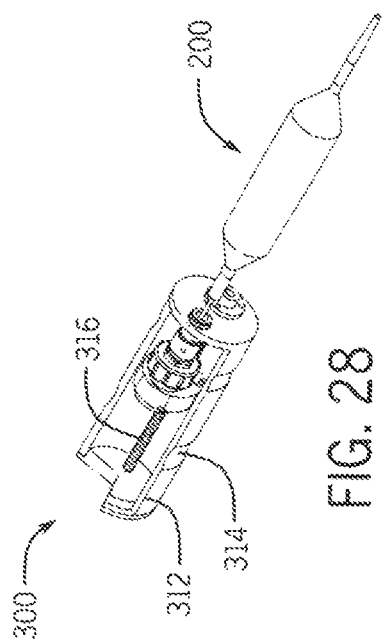

ESOPHAGEAL ABLATION TECHNOLOGY

CROSS-REFERENCE TO RELATED APPLICATIONS, IF ANY

This application is a Continuation-in-Part of U.S. patent application Ser. No. 15/486,078, filed Apr. 12, 2017, now abandoned, which claims the benefit under 35 U.S.C. § 119(e) of U.S. Provisional Patent Application Ser. No. 62/321,239, filed Apr. 12, 2016, which is hereby incorporated by reference.

37 C.F.R. § 1.71(e) AUTHORIZATION

A portion of the disclosure of this patent document contains material which is subject to copyright protection. The copyright owner has no objection to the facsimile reproduction by anyone of the patent document or the patent disclosure, as it appears in the US Patent and Trademark Office patent file or records, but otherwise reserves all copyright rights whatsoever.

STATEMENT REGARDING FEDERALLY SPONSORED RESEARCH OR DEVELOPMENT

Not applicable.

REFERENCE TO A MICROFICHE APPENDIX, IF ANY

Not applicable.

BACKGROUND OF THE INVENTION

1. Field of the Invention

The present invention relates, generally, to ablation systems, apparatus and methods. Particularly, the invention relates to a thermal ablation device and method for treating abnormal tissue in the esophagus. More particularly, the invention relates to a device and method for use in treatments for Barrett's Esophagus, Esophageal Adenocarcinoma, Esophageal Squamous Cell Carcinoma, and the like. Most particularly, the invention relates to a positioner for a device used in treating Barrett's Esophagus, Esophageal Adenocarcinoma, Esophageal Squamous Cell Carcinoma, and the like.

2. Background Information

Barrett's esophagus is a condition in which tissue in the esophagus (a tube connecting the mouth and stomach) is replaced by tissue similar to the stomach lining. It is often diagnosed in persons who have long term gastroesophageal reflux disease (GERD). It is associated with an increased risk of developing esophageal cancer. Treatment includes management of GERD, drug therapy, and laser therapy. Treatment also includes balloon-based radio frequency ablation.

Esophageal adenocarcinoma and Esophageal squamous cell carcinoma are forms of esophageal cancer that occurs in the esophagus. Treatment typically involves chemotherapy, radiation and surgery.

Existing technology in this field is believed to have significant limitations and shortcomings. For this and other reasons, a need exists for the present invention.

US Patent Application 2012/0143180 (Lee et al.) discloses a microwave antenna housed within a balloon for treatment of Barrett's esophagus and to keep the antenna in the center of the esophagus.

2010/0168727 (Hancock et al.) discloses a balloon device for delivery of microwave radiation to the esophagus.

U.S. Pat. No. 8,442,645 (Zelickson et al.) discloses a balloon encapsulating an energy transmitting device for treatment of esophageal tissue.

U.S. Pat. No. 7,530,979 (Ganz et al.) discloses a device including a balloon member for application of microwave energy to treat Barrett's esophagus.

U.S. Pat. No. 6,846,312 (Edwards et al.) discloses a GERD treatment device having an expandable member with a microwave energy source.

U.S. Pat. No. 6,238,392 (Long) discloses a bipolar electrosurgical device for treatment of Barrett's esophagus using RF ablation and a balloon electrode.

U.S. Pat. No. 6,230,060 (Mawhinney) discloses a medical device with a balloon structure enclosing a microwave antenna.

All US patents and patent applications, and all other published documents mentioned anywhere in this application are incorporated by reference in their entirety.

BRIEF SUMMARY OF THE INVENTION

The invention provides a thermal, esophageal ablation, apparatus and method which are safe and effective, and which are believed to fulfill a need and to constitute an improvement over the background technology.

In one aspect, the invention provides a microwave thermal ablation system for human medical therapy, comprising:
  a microwave generator;
  at least one microwave emitter communicatively connected to the microwave generator, the microwave emitter being adapted to being inserted into the body of a patient;
  a medical balloon inflation means; and
  a positioning balloon connected to the balloon inflation means and to the at least one microwave emitter for holding the at least one microwave emitter in a desired position relative to a target tissue or tissues within the body of a patient.

In another, narrower, aspect, the invention provides a microwave thermal ablation system for use in treating Barrett's Esophageal cells via non-contact dielectric heating, comprising:
  a. a microwave generator for providing preferably 17-18 GHz microwave energy;
  b. at least one microwave emitter communicatively connected to the microwave generator, the microwave emitter being adapted to being-inserted into the body of a patient;
  c. a medical balloon inflation means;
  d. a positioning balloon connected to the balloon inflation means and to the at least one microwave emitter for holding the at least one microwave emitter in a desired position relative to a target tissue or tissues within the body of a patient, the positioning balloon being disposed around the at least one microwave emitter; and
  e. a catheter shall including:
    (i) at least one power line electrically connecting the microwave emitter and the at least one microwave generator, and
    (ii) at least one lumen communicatively fluidly connecting the balloon inflation means and the positioning balloon, the at least one microwave emitter and the positioning balloon being coupled to the catheter shaft at a predetermined position, the catheter shaft being adapted to being inserted into the body of a patient and for translating the at least one microwave emitter and the positioning balloon within and through the patient's body.

The aspects, features, advantages, benefits and objects of the invention will become clear to those skilled in the art by reference to the following description, claims and drawings.

BRIEF DESCRIPTION OF THE SEVERAL VIEWS OF THE DRAWING

FIG. 1 is a perspective view of a first embodiment of a thermal ablation device of the present invention, including a first embodiment of a positioner handle assembly therefor.

FIG. 2 is a detailed view of a distal portion of the device.

FIG. 3 is a cross-sectional view of a portion of the device taken along line 3-3 of FIG. 2.

FIG. 5 is a schematic of an embodiment of the handset of FIG. 1 with a microwave generator and a gas supply.

FIG. 11 is a side elevation view of a fourth embodiment of the device of the invention, including a balloon in an expanded state.

FIG. 12 is an elevation view of the device showing certain internal components thereof in phantom in an expanded or actuated state.

FIG. 15 is a side elevation view of the scaffolding assembly and antennas of the device in a collapsed state.

FIG. 16 is an opposite side elevation view of the scaffolding assembly.

FIG. 17 is an end view of the scaffolding assembly.

FIG. 18 is a side elevation view of the scaffolding assembly and antennas of the device in an expanded state.

FIG. 19 is an opposite side elevation view of the scaffolding assembly.

FIG. 20 is an end view of the scaffolding assembly.

FIG. 21 is a side elevation view of a fifth embodiment of the device of the invention, including an external balloon in an expanded state.

FIG. 22 is an elevation view of the device showing certain internal components thereof in phantom, including an internal balloon and antennas in an expanded or actuated state

FIG. 25 is a side elevation of an embodiment of the device including the balloon assembly, of FIGS. 21-24, and an embodiment of a positioner assembly therefor.

FIG. 26 is a detailed view of the balloon assembly, with internal components visible.

FIG. 27 is a detailed view of the handle assembly.

FIG. 28 is an isometric view of the system of FIG. 25.

DETAILED DESCRIPTION

Figure 4:
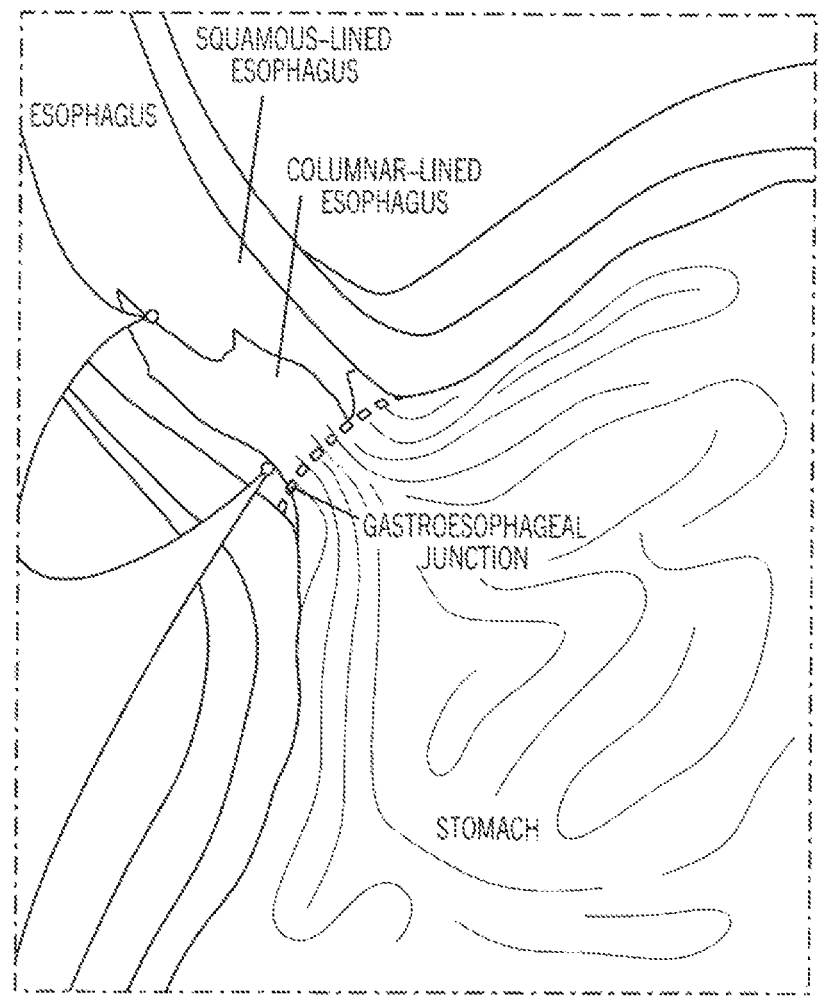
FIG. 4 is an illustration of the anatomy of a patient with Barrett's' esophagus.

The present invention provides a system, device and method for treating abnormal tissue in the esophagus. The invention is useful for treating Barrett's esophagus, esophageal adenocarcinoma, esophageal squamous cell carcinoma, and the like. The invention functions, in general, via ablation and particularly thermal ablation. The system preferably uses microwave power.

FIGS. 1-3 show a first embodiment of the esophageal ablation system of the present invention. The system 10 comprises a handset including an elongated, flexible shaft 11 and an emitter assembly 12 at the terminal, distal end of the shaft 11. The system preferably includes at embodiment of a hand piece type positioner 13 which is manipulated by a user to insert and steer the shaft 11 and emitter assembly 12 into and through the mouth and esophagus of a patient. The hand piece 13 has a connection end 14 for communicative mating with fluid systems and power systems. The hand piece 13 also has a distal end 15 from which the shaft 11 extends.

Referring also to FIGS. 2 and 3, the elongated, flexible shaft 11 comprises a central power cable 20, which is preferably coaxially surrounded by an inner layer 21 and an outer layer 22. The power cable 20 conducts microwave power from a power generator (shown in FIG. 5 and discussed below) to the emitter assembly 12. An outer lumen 23 is formed between the outer layer 22 and the inner layer 21, and permits inflow of fluids (air, gas, water or other liquids) used to actuate an optional balloon. An inner lumen 24 formed between the inner layer 21 and the power cable 20 permits outflow of fluids in embodiments where a balloon is used. Inflow terminates at orifice 25. Outflow initiates at orifice 26. The shaft 11 has a predetermined preferred length and outside diameter. Flow is preferably reversible.

Referring to FIG. 2, the emitter assembly 12 comprises at least one emitter antenna 30 which is communicatively connected to the distal, terminal end of the power cable 20. The emitter antenna emits microwave radiation to target tissues selected by the user clinician. The emitter 30 is preferably a broadband emitter capable of emitting a range of microwave frequencies and phases. The emitter may alternatively be a narrow-band antenna. Preferably, the antenna structurally is a coaxial antenna, patch antenna or planar antenna array. It is within the purview of the invention that the antenna may alternatively have a tri-axial, slot, helical, bow-tie, dipole or a multi-array antenna structure. The emitter may be positioned laterally, longitudinally or rotationally via the shaft 11. Additionally, the emitter may be moved in 3 dimensions during actuation. Energy may be emitted circumferentially.

During microwave emission, the antenna 30 is preferably spaced apart from the target tissue a predetermined distance. This provides non-contact dielectric heating of the tissue. The balloon 40 is preferably used for such positioning. The balloon 40 is inflated and deflated by fluid conducted to and from the inlet and outlet lumens 23 and 24. The balloon 40 may be used to position the emitter 30 centrally or off center in the esophagus relative to target tissue. The balloon 40 may be compliant, non-compliant or semi-compliant. In one embodiment, the balloon has a length of 10-60 mm, and a diameter of 14-40 mm. The balloon 40 is preferably constructed of a transparent material to permit visualization of positioning by the user via an endoscope or the like. Visualisation may be made before or during emitter actuation. The device preferably has visual indicator to show target ablation zone. This could be a marking on the outer balloon such as an outline of the target ablation zone. Alternatively, it may take the form of an optical cue such as an LED/laser projection on to target ablation zone. Alternatively, or additionally, the distance from the emitter 30 to the target tissue may be detected via microwave topography. The balloon's surface may include one or more shielded areas that permit or inhibit microwave transmission to control ablation. Further, the shielding may be adjustable by the user during a procedure.

In the embodiment shown the balloon 40 and emitter 30 are fixed in position relative to each other. It is within the purview of the invention that the position of the balloon 40 and emitter 30 may be varied and may be adjustable.

It is within the purview of the invention that multiple emitters may be used with the system. And although the embodiment of the system includes a balloon to position the emitter relative to the target tissue, it is also within the purview of the invention that other means of spacing may be used, including other expandable/retractable devices or assemblies. Further, the position of multiple emitters may be adjusted (rotationally, laterally and longitudinally) relative to each other. And, the emitters may be actuated independently from each other.

An alternative version of the embodiment discussed above, the hand set 10 includes a temperature sensor such as a thermocouple, thermistor, optical temperature sensor, or the like to measure tissue temperature. Alternatively, tissue properties may be measured via radiometric sensing using the emitter 30 as a receiver.

Referring to FIG. 5, the handset 10 is correctable to a microwave generator 16. The generator 16 may provide variable frequency, phase and power duty cycle to modify the thermal profile of the tissue and to control the depth of penetration of energy into the tissue. In one embodiment, the generator 16 provides a 17-18 GHz frequency range. A gas supply 17 is also connected to the handset 10. The gas supply may comprise a pump and/or a control valve connected to a source of gas. Alternatively, the gas supply 17 may be integrated with the generator 16.

Figure 7A:
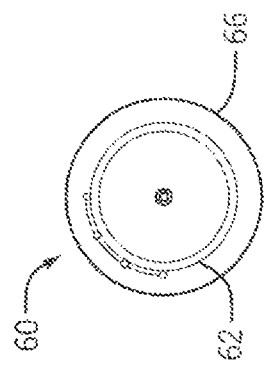
FIGS. 7A-C are proximal end, side elevation, and distal end views, respectively, of the embodiment of FIGS. 6A-F, including an outer positioning balloon, also deployed, and in phantom to show the relationship of internal elements.
Figure 6D:
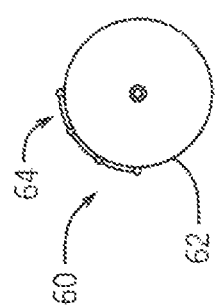
FIGS. 6D-F are proximal end, side elevation, and distal end views, respectively, of the embodiment shown in FIGS. 6A-C, with surface shading.
Figure 6A:
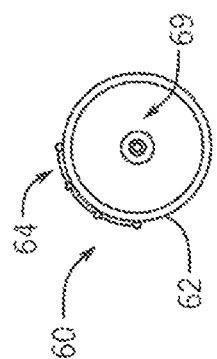
FIGS. 6A-C are proximal end, side elevation, and distal end views, respectively, of a second embodiment of the thermal ablation device, including a deployable antenna array with an inner deployment balloon both shown in a deployed state.
Figure 7B:
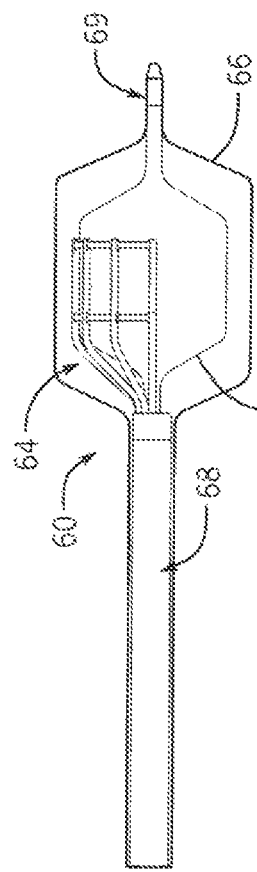
Figure 6E:
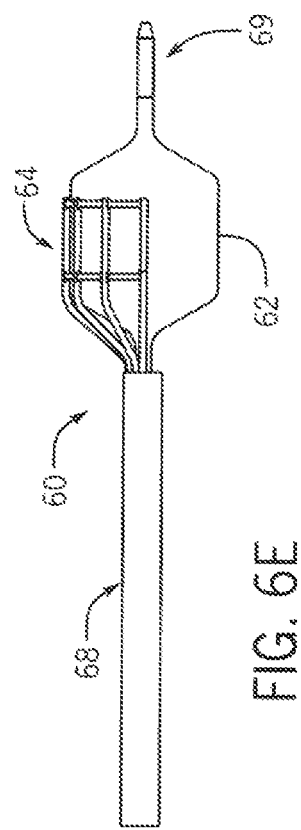
Figure 6B:
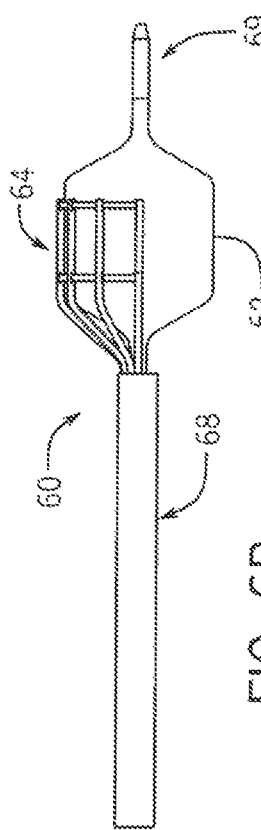
Figure 7C:
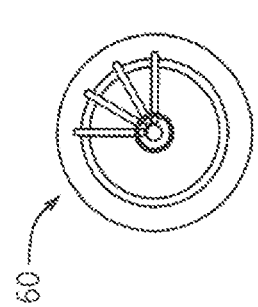
Figure 6F:
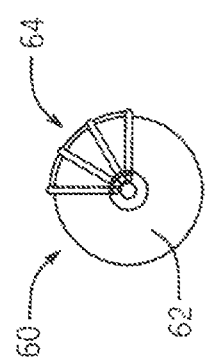
Figure 6C:
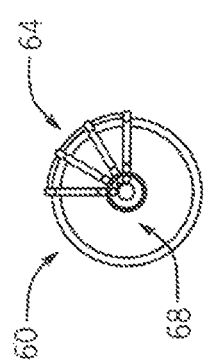

FIGS. 6 and 7 show a second embodiment of the device 60 of the invention with a compliant inner deployment balloon 62, an antenna array 64 mounted there over and with fixed, angular spacing, and a compliant outer positioning balloon 66. The device 60 also has a proximal shaft assembly 68 and a distal tip assembly 69. The inner balloon 62 diameter may be controllable to fix or optimize the distance between the antenna 64 and the ablation target. The antenna array is rotatable from the handle to enable circumferential ablation. The antenna 64 struts constrain the are length between adjacent antennas. This maintains the distance between antennas thereby fixing the amount of overlap between electric fields. The overlap is constant over a full diameter range.

Alternatively, the antennas may also be constructed and arranged in a linear array to cover a greater axial distance. Lastly, it is within the purview of the invention that the device 50 could be constructed of a self-expanding scaffold antenna array, thereby obviating the inner balloon 62.

Figure 8:
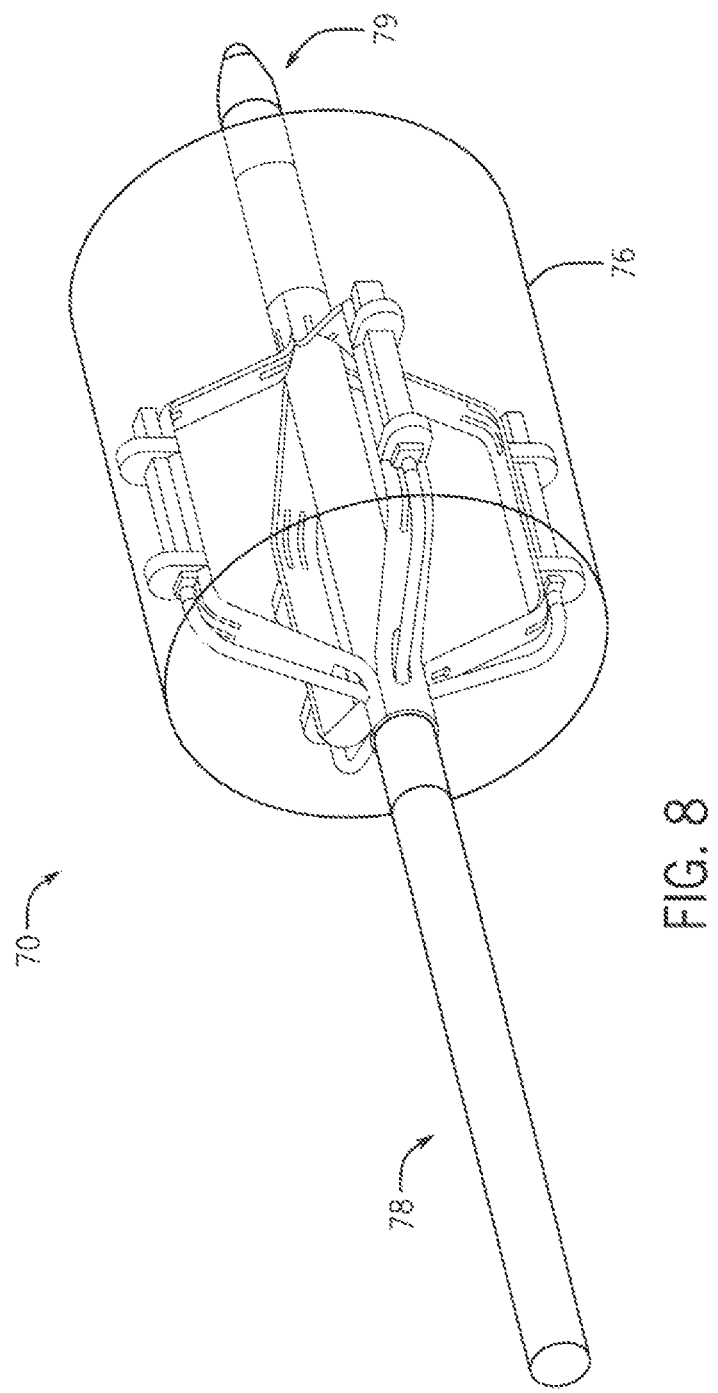
FIG. 8 is a perspective view, partially in phantom to reveal interior elements, of a third embodiment of the thermal ablation device.
Figure 10A:
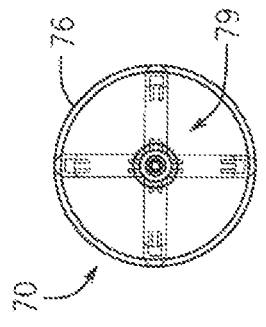
FIGS. 10A-C are proximal end, side elevation, and distal end views, respectively, of the embodiment of FIGS. 9A-F, including an outer positioning balloon, also deployed, and in phantom to show the relationship of layered elements.
Figure 10B:
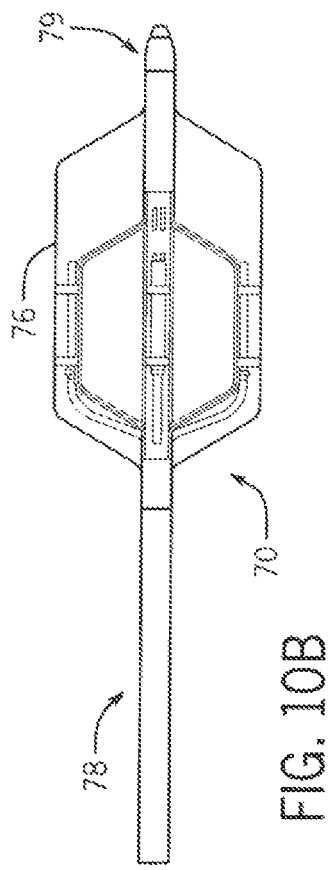
Figure 9A:
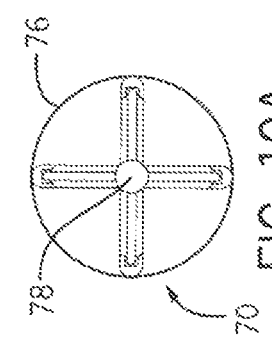
FIGS. 9A-C are proximal end, side elevation, and distal end views, respectively of the device of FIG. 8, with another embodiment of an antenna array and an inner deployment balloon, showed deployed.
Figure 9D:
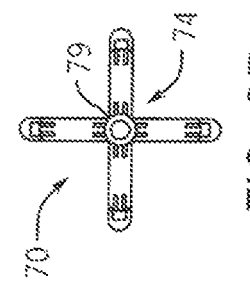
FIGS. 9D-F are views similar to those shown in FIGS. 9A-C, with surface shading.
Figure 9E:
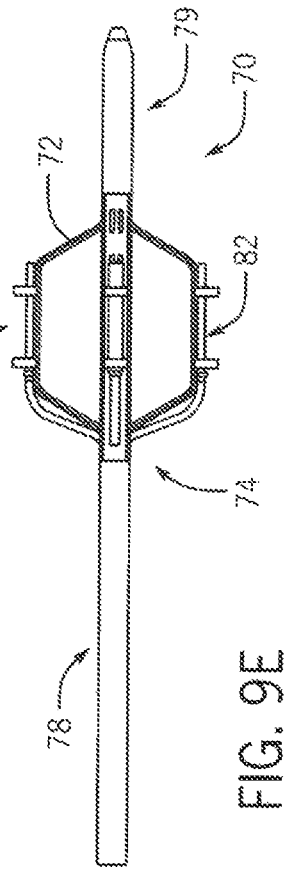
Figure 9B:
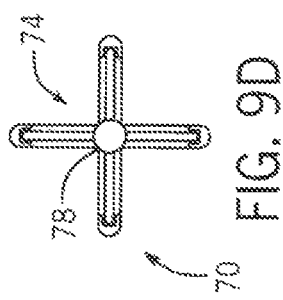
Figure 10C:
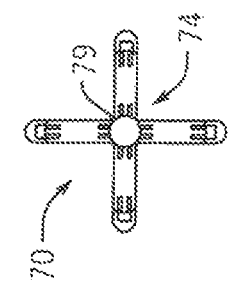
Figure 9F:
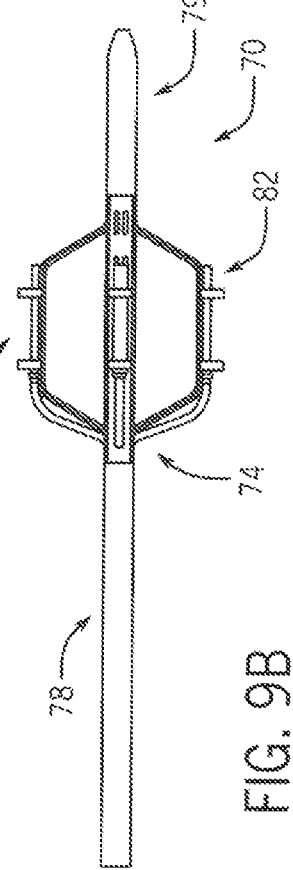
Figure 9C:
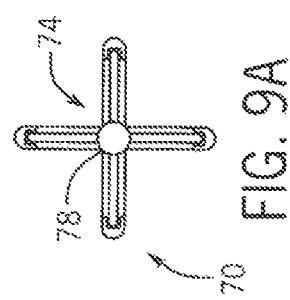

FIGS. 8-10 show a third embodiment of the device 70 of the invention featuring planar scaffold guides 82. The device 70 has a compliant inner deployment balloon 72, an array of four (4) antennas 74 mounted there over and with fixed angular spacing, and a compliant outer positioning balloon 76. The device 70 also has a proximal shaft assembly 78 and a distal tip assembly 79. This embodiment 70 has four antennas in a radial array. It is believed to be optimal, however, from 2 to 12 antennas may be used to practice the principles of the invention. Multiple antennas may be activated at once. Or, a single antenna may have activated to ablate a narrow patch of target tissue.

This device 70 may also use a self-expanding, or mechanically expandable (controlled from the handle) antenna array. However, the use of an inner balloon 72 is believed to be advantageous because the inflation fluid can be controlled and the dielectric properties of the fluid chosen for inflation modified to control ablation. A linear array may also be used to cover a greater axial surface in certain circumstances.

Referring to FIGS. 11-14, a fourth embodiment of the device 100 comprising a balloon 112 attached proximally to an outer shaft 114 and distally to a tip 116 with a thru lumen 118. The balloon 112 is preferably constructed of urethane. The balloon 112 is shown in an expanded state. It can expand to accommodate the full range of esophagi lumen diameters. The urethane balloon 112 is preferably inflated with air. The function of the urethane balloon 112 and outer shaft 114 is to create a deterministic circular lumen of known diameter inside the esophagus of a patient. The outer shaft 114 is connected to a handle and allows for the insertion of the entire assembly 110 down the month of the patient to the target in the esophagus. Exemplary handles embodiments are shown in FIGS. 1, 25 and 28.

Figure 13:
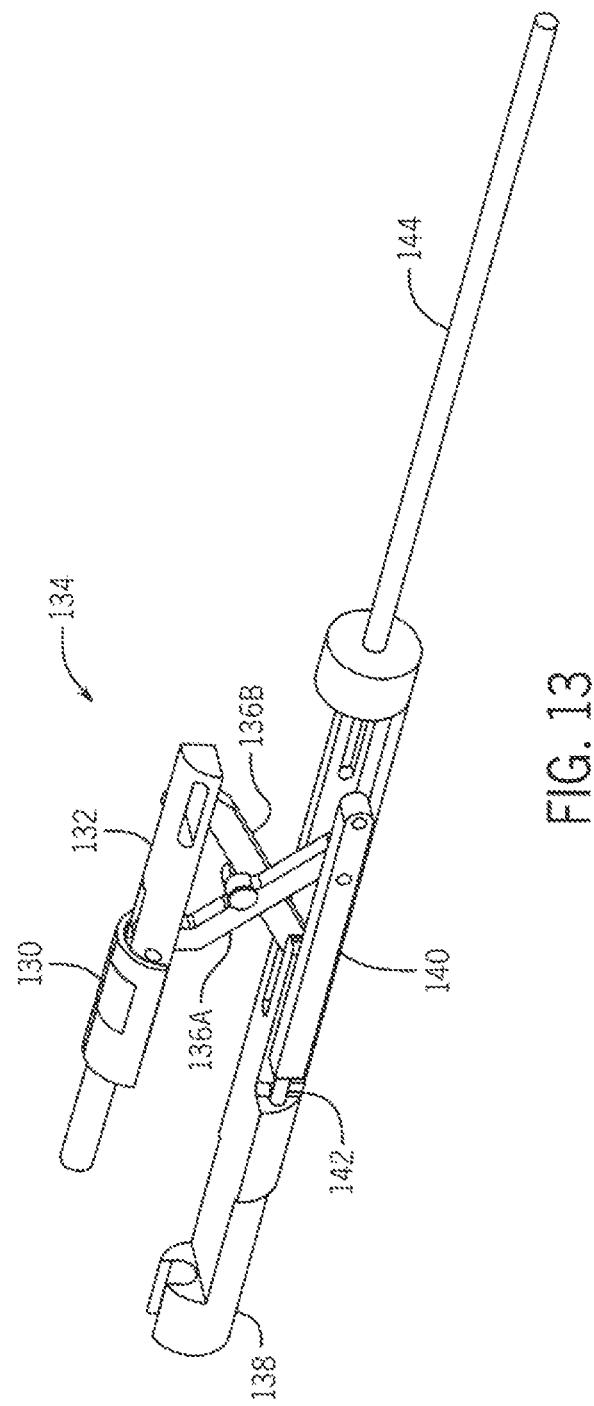
FIG. 13 is an isometric view of certain internal components of the device in an actuated state.
Figure 14:
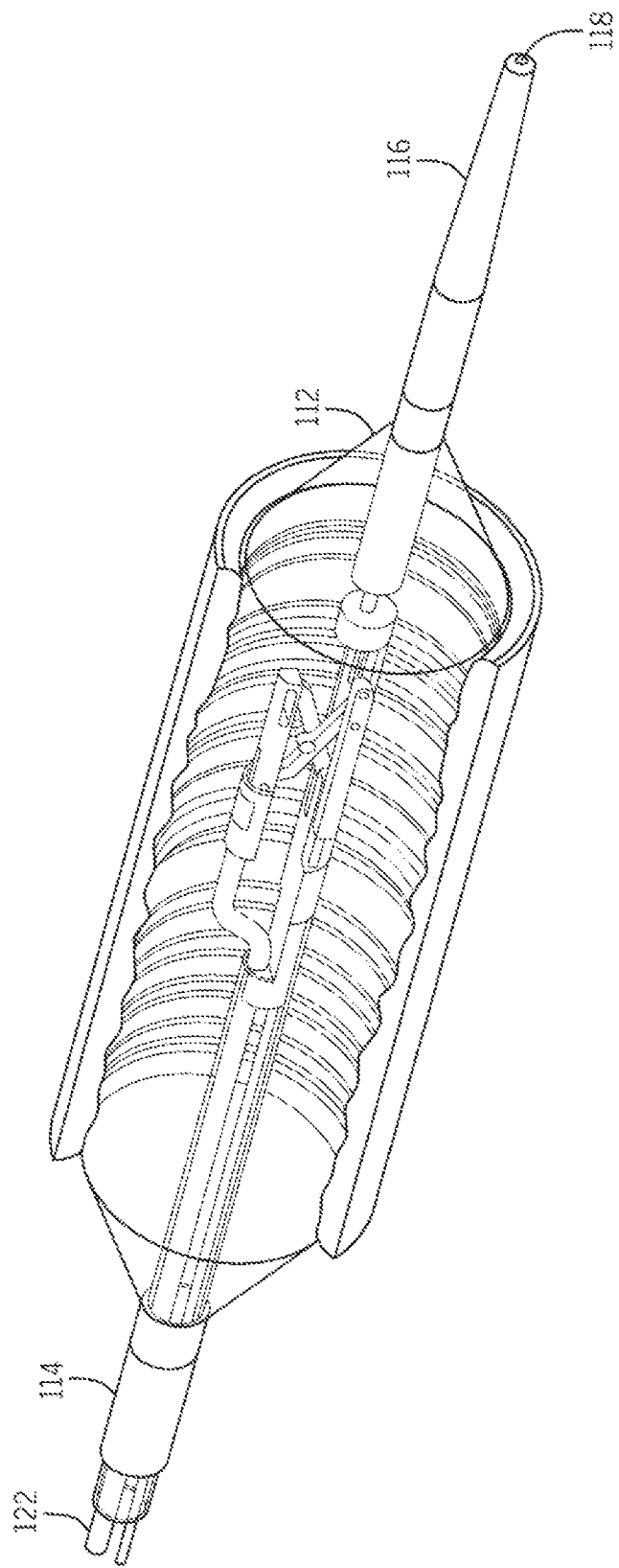
FIG. 14 is an isometric view of the device showing the device operatively disposed in the esophagus of a patient.

As is best shown in FIGS. 12-14, inside the balloon 112 and outer shaft 114 is an inner shaft 120. The inner shaft 120 contains a coaxial cable 122 and a pull wire 124. The coaxial cable 122 connects to an antenna or emitter 130. The connection is preferably a solder connection. The microwave antenna 130 is preferably a direct fed, patch type antenna that is curved around a radius. Applicants have found that curving provides mechanical advantages, and also increases the ablation zone. The antenna 130 is designed to operate preferably between 17-18 GHz. The antenna 130 and coaxial cable 122 assembly is soldered to an antenna mount 132. Referring also to FIGS. 15-26, the antenna mount 132 connects to a scaffold assembly via expansion links 136 A and B. The antenna mount 132 also serves as a transition from the coaxial cable 122 to the antenna 130. This arrangement maximizes energy transfer from the cable 122 to the antenna 130 and reduces reflected power. The expansion links 136 attach to a centering/bottom link 138 and a pull link 140. The pull link 140 further connects to a pull wire 142 or mandrel. The pull wire 142 connects to a mechanism in the handle that creates the expansion and contraction of the scaffold assembly 134 and allows the user to position the antenna 130 at the correct offset from the tissue which will result in the most, efficient heating of the target tissues.

The bottom/centering link 138 keeps the entire antenna assembly 130 on centerline. A telescoping shaft 144 inserts into the through lumen 118 of the outer balloon tip 116. This allows the user to rotate the antenna assembly 360° for circumferential ablations and also traverse the antenna assembly 130 longitudinally along the axis of the esophagus so that the user can perform ablations along the length of the esophagus.

It is within the purview of the invention that all mechanical movements (rotation, scaffold expansion/contraction, longitudinal movement) can be automated through the use of motors (not shown).

The most preferred frequency range of 17-18 GHz limits the depth of penetration of the ablation zone to the first 1.5 mm of tissue, which is desired for treatment of Barrett's Esophagus. Modulating input power and dwell time can further control depth of ablation.

Figure 23:
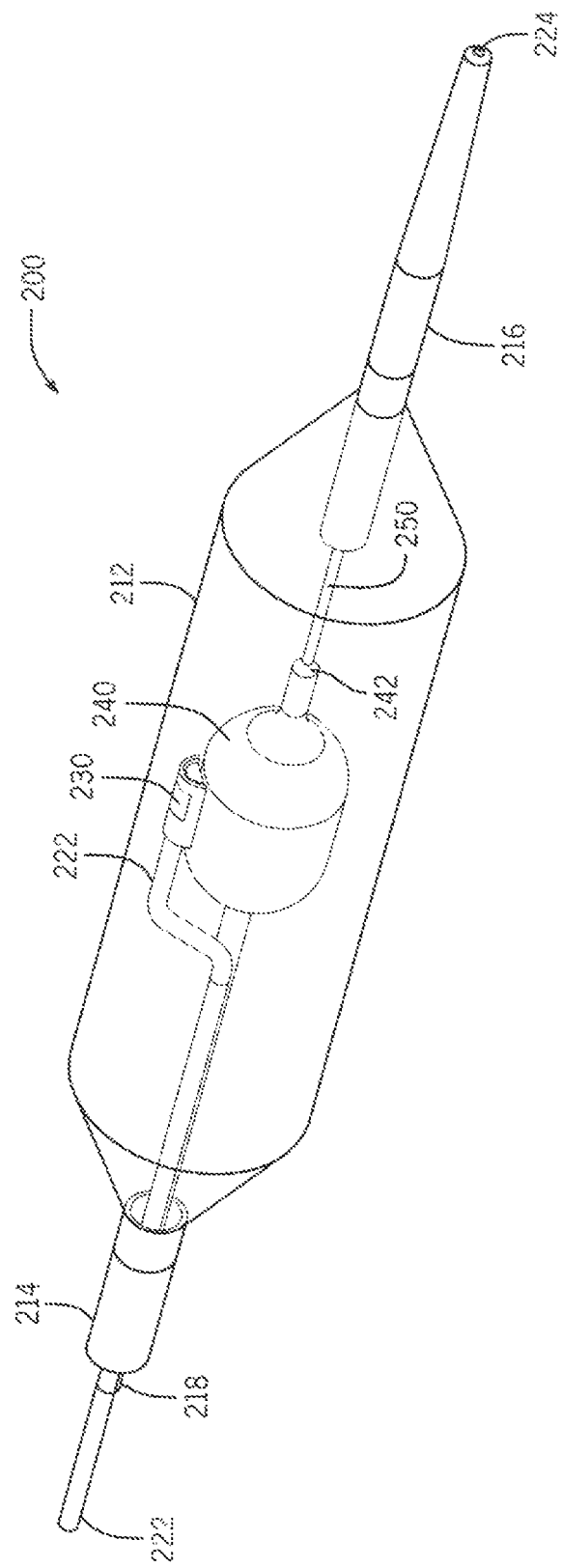
FIG. 23 is an isometric view of the device showing the device.

Referring to FIGS. 21-23, a fifth embodiment of a device 200 of the invention comprises a balloon 212 connected proximally to an outer shaft 214 and distally to a tip 218 assembly. This balloon 212 is also preferably constructed of urethane. The functions of these elements are substantially the same the same as similar structures in the previous embodiment of FIGS. 11-20.

Inside the outer balloon 212 and outer shaft 214 is an inner shaft 218, which consists of two lumens. A coaxial cable 222 extends through the first lumen. The second lumen is used to push saline through to inflate the balloon 212. The coaxial cable 222 emerges through the inner shaft 218 and attaches to an antenna 230. The antenna 230 preferably has the same structure and function as the antenna described and shown in the previous embodiment of FIGS. 11-20. The antenna 230 and coaxial cable 222 assembly once again is attached to an antenna mount 232, which serves the same purpose of efficiently transferring energy from the cable 222 to the antenna 230.

Figure 24:
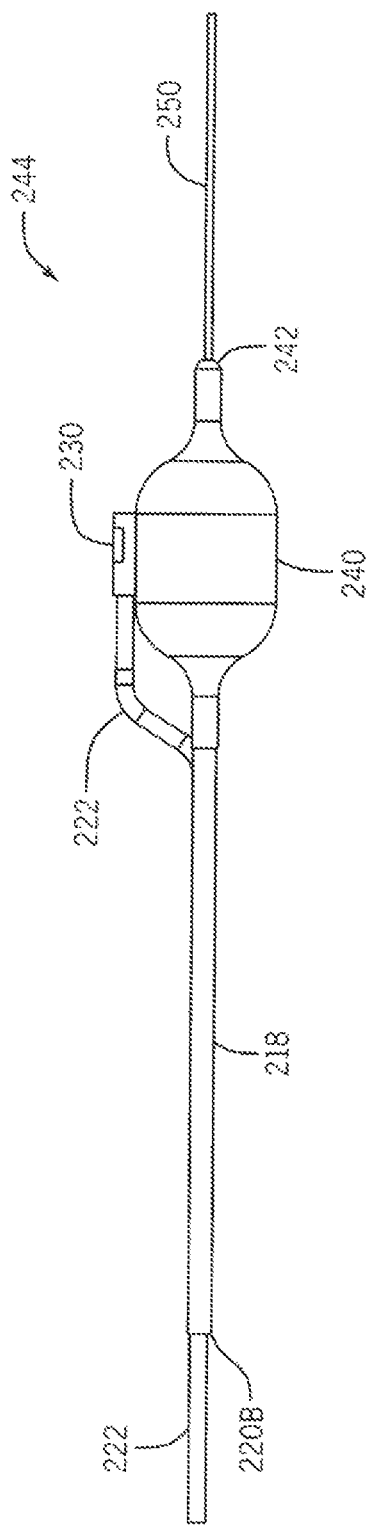
FIG. 24 is an isometric view of certain internal components of the device.

Referring also to FIG. 24, attached to the distal end of the inner shaft 218 is an inner, semi-compliant balloon 240. The inner balloon 240 is capable of multiple diametrical positions over a total diameter range increase of 1 mm-5 mm growth. The antenna mount 233 is also attached to the balloon 240. The inner balloon 240 replaces the mechanical scaffold from the previous embodiment. The balloon 240 is inflated with saline, and depending on the input pressure of the fluid, it will expand to a deterministic diameter. This permits the user to deliver the antenna 230 to the correct offset from the target tissue.

The semi-compliant balloon 240 is distally attached to the telescoping tip/shaft 250. The telescoping shaft 250 inserts into the through lumen 224 of the outer balloon tip 216. This allows the user to rotate the antenna assembly 230 360° for circumferential ablations and also traverse the antenna assembly 230 longitudinally along the axis of the esophagus so that the user can perform ablations along the length of the esophagus.

Once again, all the mechanical actions can be adapted to be fully automated. Motors can rotate and longitudinally move the inner shaft assembly. Further, an automated pump can be constructed and arranged inflate the inner, semi-compliant balloon 240 with saline to the correct diameter.

FIGS. 25-28 show an embodiment of the system 300 including the emitter assembly 200 described above with an alternative embodiment of a handle assembly 310. The handle assembly 310 includes a handle body 312 with a cavity in which is disposed a thumb wheel 320 for rotating the inner balloon 240 of the emitter 200. The thumb wheel 320 is connected at one end to an SMC push to connect rotary fitting 322. A rotating connector is disposed at the opposite end of the thumb wheel 320 for connection to an antenna power cable. A ball screw 316 provides precise longitudinal movement. The handle body 312 preferably has ergonomic grooves to facilitate optimal manual manipulation by the user.

Figure 29:
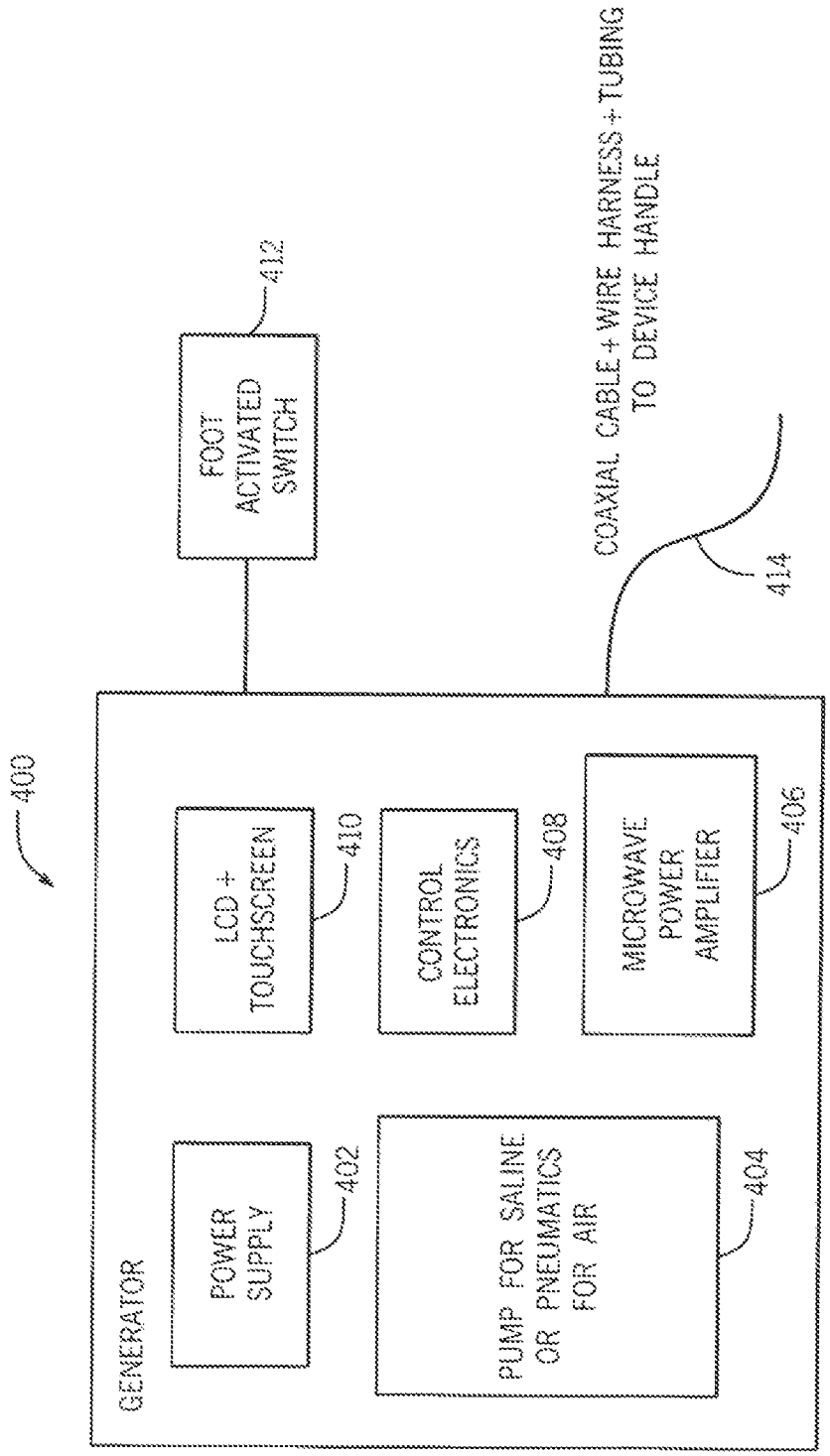
FIG. 29 illustrates an embodiment of a generator assembly useable with the system of the invention.
Figure 30:
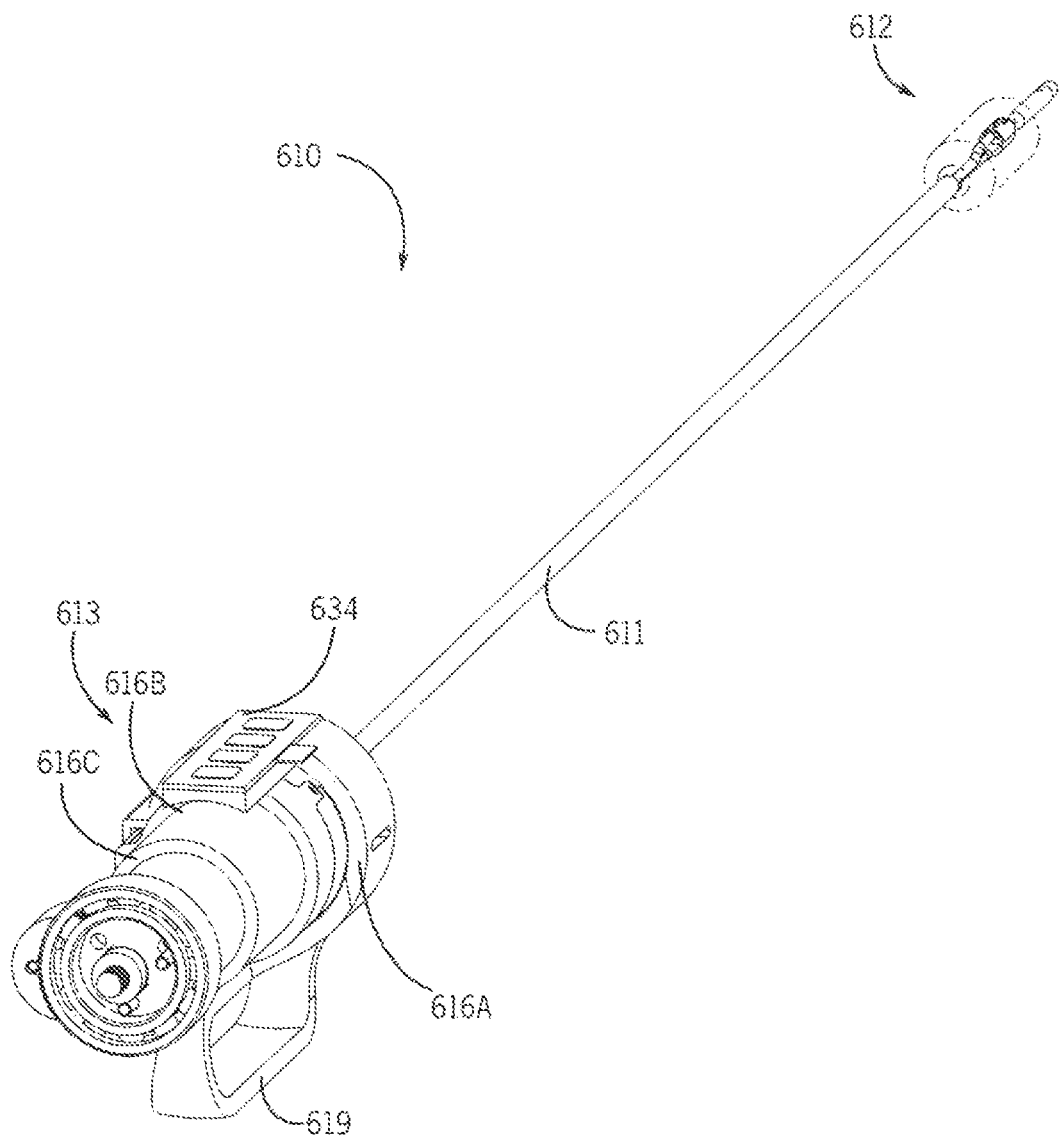
FIG. 30 is a perspective view of a sixth embodiment of the device of the invention, including an second embodiment of a handle or positioner.

FIG. 29 shows an embodiment of a control assembly 400. The control assembly 400 comprises a power supply 402 communicatively connected to a controller 408 containing control electronics. A pump 404 and microwave power amplifier 400 are communicatively connected to the controller 408. The pump 404 delivers fluid (such as Saline) or gas (such as air) for hydraulic or pneumatic control of the balloons of the emitter assembly 200. The amplifier 406 powers the antenna of the emitter 200. The amplifier 406 operates in a frequency range of 915 MHz to 20 GHz. Preferred operating frequencies are 2.45 GHz, 5 GHz and 17-18 GHz. Presently, the most preferred frequency is approximately 18 GHz. Hydraulics, pneumatics and microwave power are provided via a wiring harness 414 containing applicable coaxial cable, wiring and tubing, preferably via a system handle 13 or 310 discussed above. User interface controls such as an LCD Touch Screen monitor and input 410 and/or a foot activated switch 412 are preferably communicatively connected to the controller 408.

FIGS. 30 and 32-36 show a sixth embodiment of the device or system 610 of the invention including an embodiment of a handle, positioner or handset therefor. This device embodiment 610 contains many of the features and functions of the previous embodiments such as a microwave antenna 630 mounted on a semi-compliant inner balloon 640. The inner balloon 640 is used to position the antenna 630 at the correct offset from the target tissue. This assembly is inside an outer balloon 641 that creates the circular lumen inside the esophagus.

Significantly, the system 610 comprises a handle, handset or positioner 613 connected to an emitter antenna assembly 612 via a shaft 611. The elongated, flexible shaft 611 comprises a central power cable 620, which is preferably coaxially surrounded by an inner cable layer 621 and an outer cable layer 622. The power cable 620 conducts microwave power preferably from the power generator 16 (shown in FIG. 5) to the emitter assembly 612.

The positioner 613 has a cylindrical three-piece body composed of three overlapping housings 616A-C. The main housing 616A is dome-shaped at the distal end of the positioner 613 and features an aperture 618 for the shaft 611 to pass through. A finger guard 619 is mounted to housing 616A by screws. The finger guard 619 provides a loop below the positioner 613 through which the fingers of the user's hand can fit to provide a stable grip. At the proximal end of the positioner 613, a coaxial connector 614 protrudes from the proximal end of housing 616C. Surrounding the coaxial connector 614 is a rolling bearing 626. A crescent shaped piece 628 is mounted to the exterior of the outer race of the hearing 626, and the crescent shaped piece 628 receives one end of a lead screw 632. The other end of the lead screw 632 is inserted through the primary housing 616A and is coupled to a motor 638 as described below.

Figure 31:
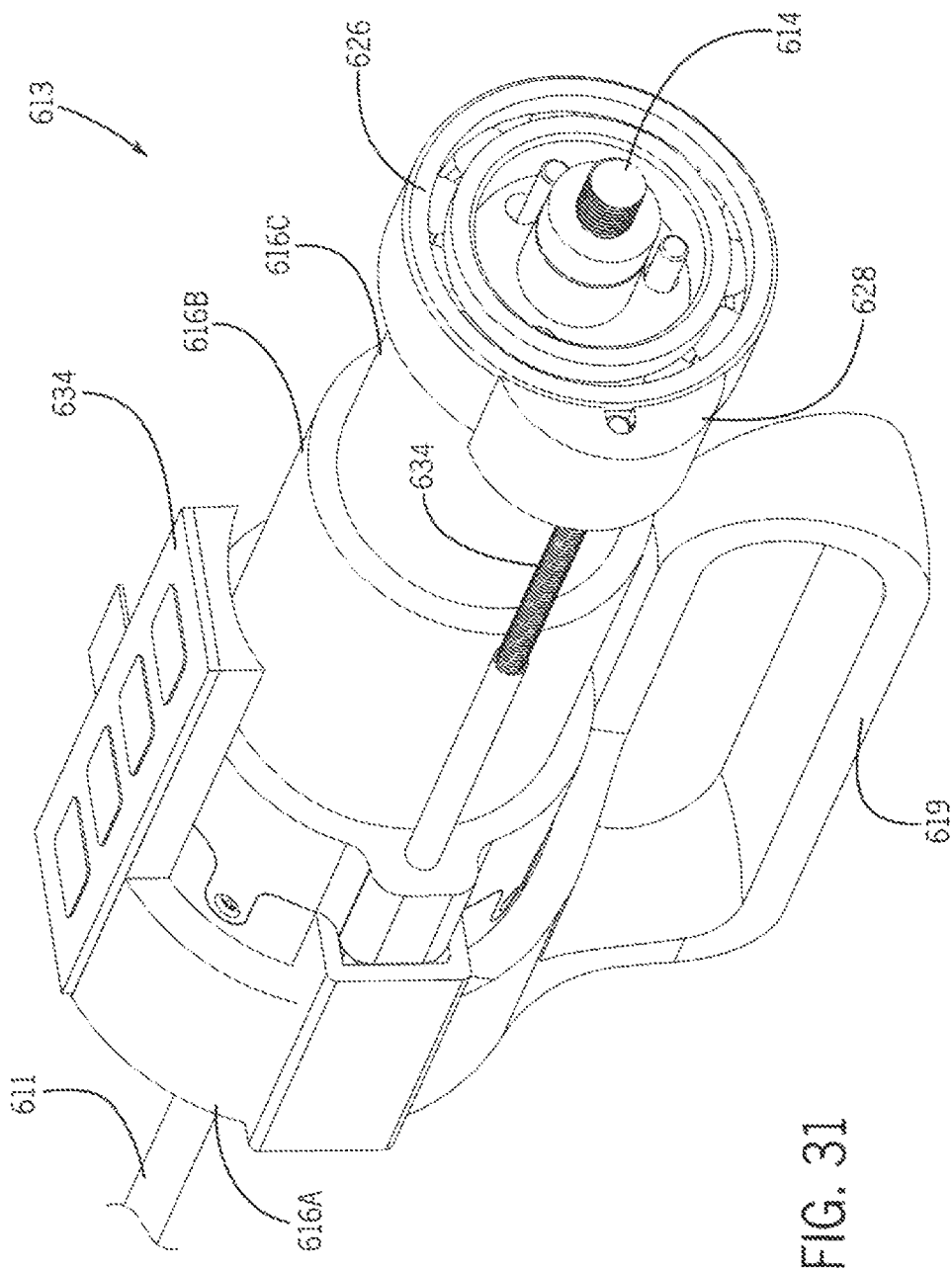
FIG. 31 is a perspective view of a proximal end of the handle or positioner of the device.
Figure 32:
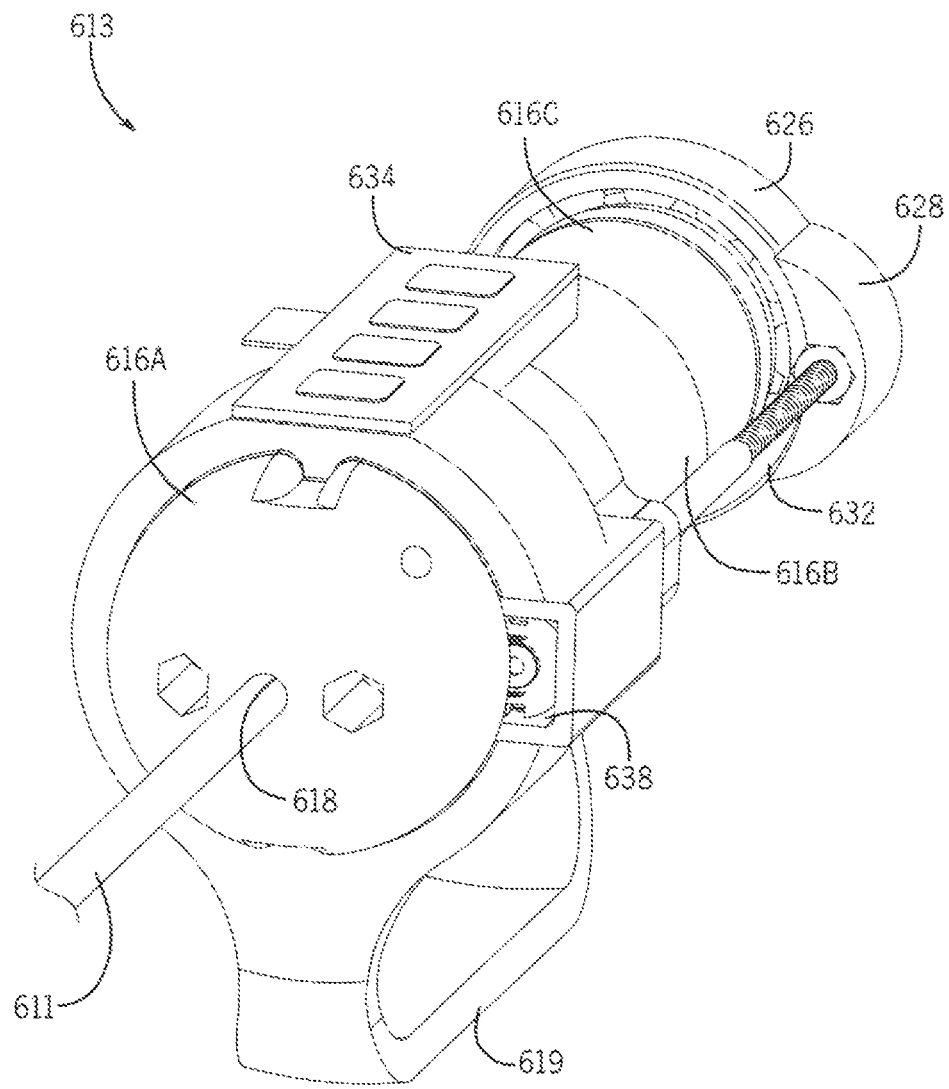
FIG. 32 is a perspective view of a distal end of the positioner.
Figure 33:
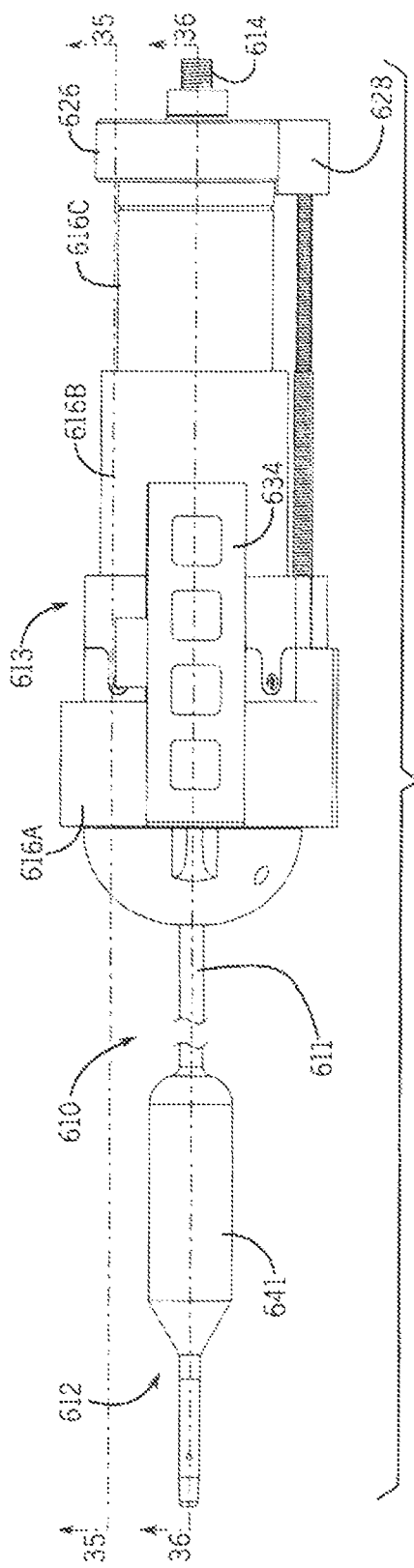
FIG. 33 is a side elevation view of the device.
Figure 34:
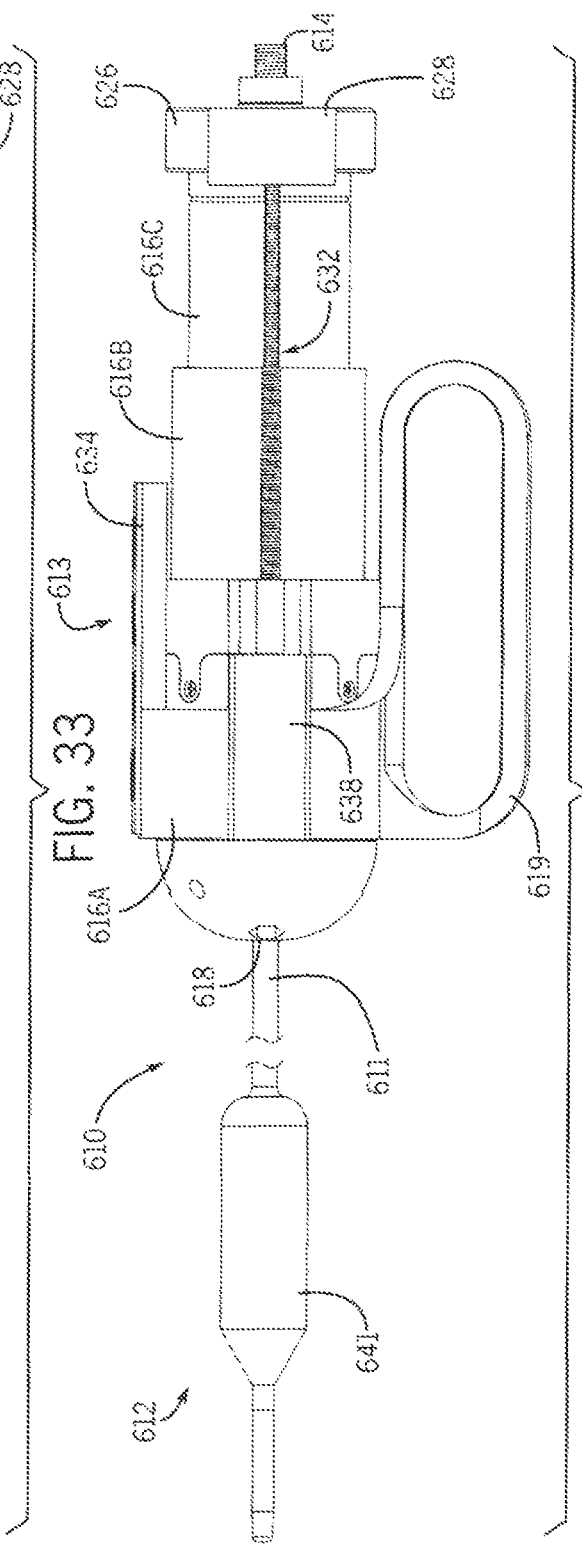
FIG. 34 is top view of the device.
Figure 35:
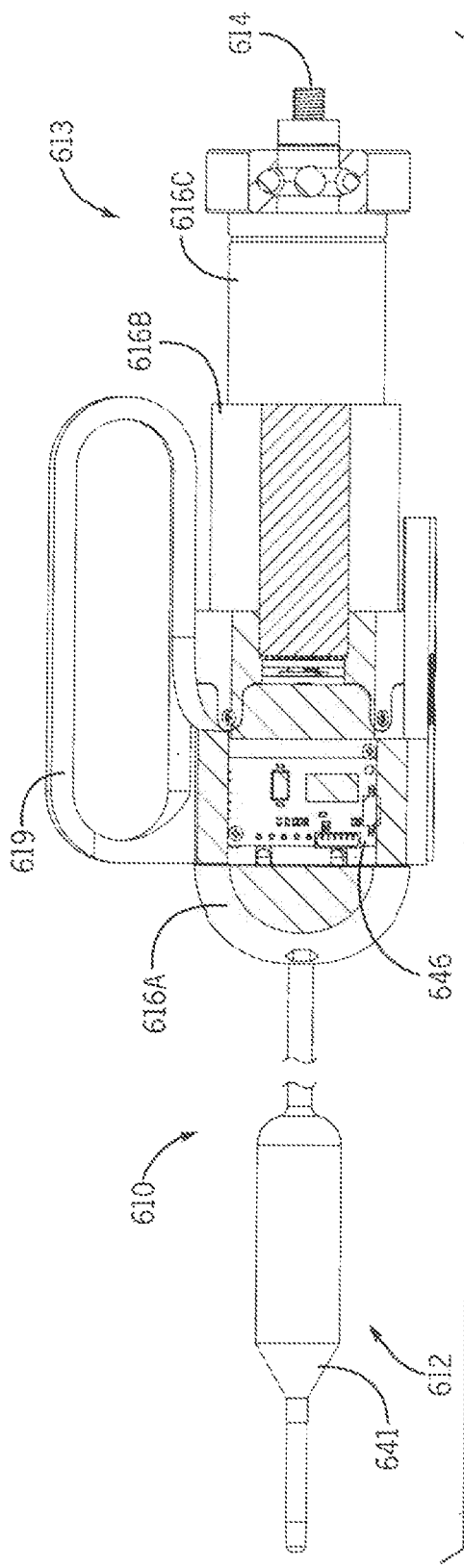
FIG. 35 is a cross-sectional view of the device, taken at Section 35-35 of FIG. 34.
Figure 36:
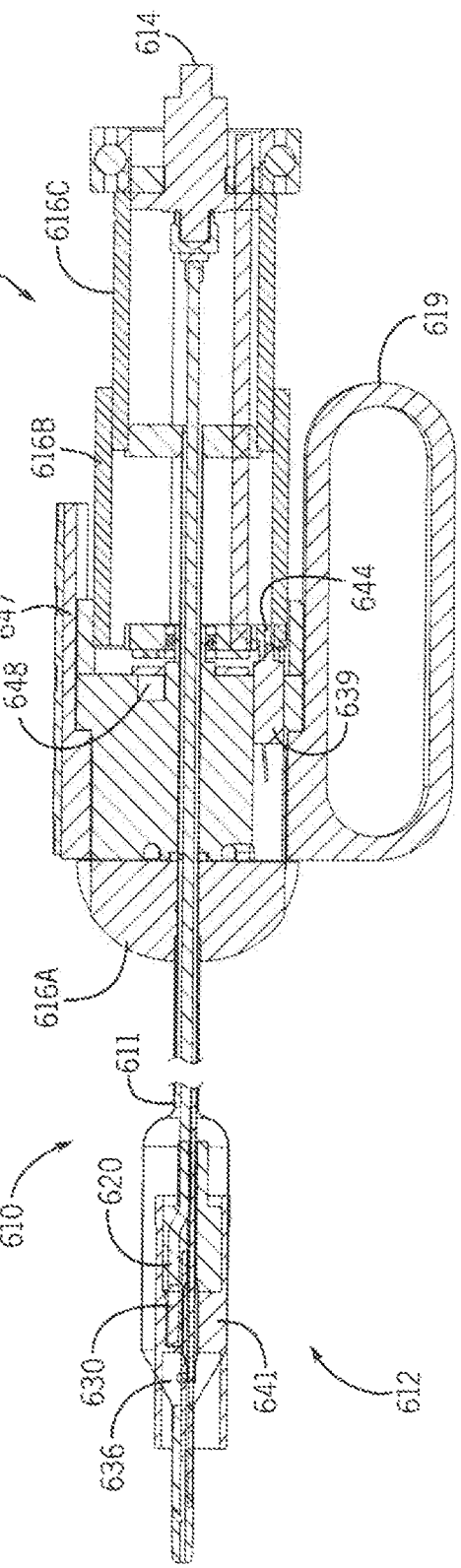
FIG. 36 is a cross-sectional view of the device, taken at Section 36-36 of FIG. 34.

Referring also to FIGS. 31 and 32, the positioner 613 includes a rectangularly shaped membrane switch keypad 634. The membrane switch keypad 634 is a set of preferably four electrical tactile switches that can be used by the physician to activate motion of the antenna assembly 612. The motion can be both rotational and longitudinal. The membrane switch 634 can also be used to activate an ablation zone indicator 636. The finger guard 619 wraps around the positioner body 613 to provide a platform for the keypad 634 on top of the main housing 616A.

Referring also to FIGS. 35, 36, 38 and 39, there are two motors 638, 639 that control motion of the antenna assembly 612. The motors 638 and 639 are preferably brushed or brushless DC motors or stepper motors. Motor 638, housed on the side of the main housing 616A, creates longitudinal or linear motion via the lead screw mechanism 632. The lead screw 632 can also be a ball screw. Motor 639 creates the rotational motion of the antenna assembly 612. The motor 639 engages a set of drive gears 642 and 644, which are communicably coupled to the shaft 611 within the positioner body 613, to rotate the antenna assembly 612.

The primary housing 616A contains the motors 642 and 644, a printed circuit board assembly 646, the lead screw mechanism 632, the rotating coaxial connector 614, a slipring or rotary joint assembly 650, and the membrane switch keypad 634. The housing 616A provides an ergonomic method to manipulate and control the device, and can be made of plastic or metal.

Figure 37:
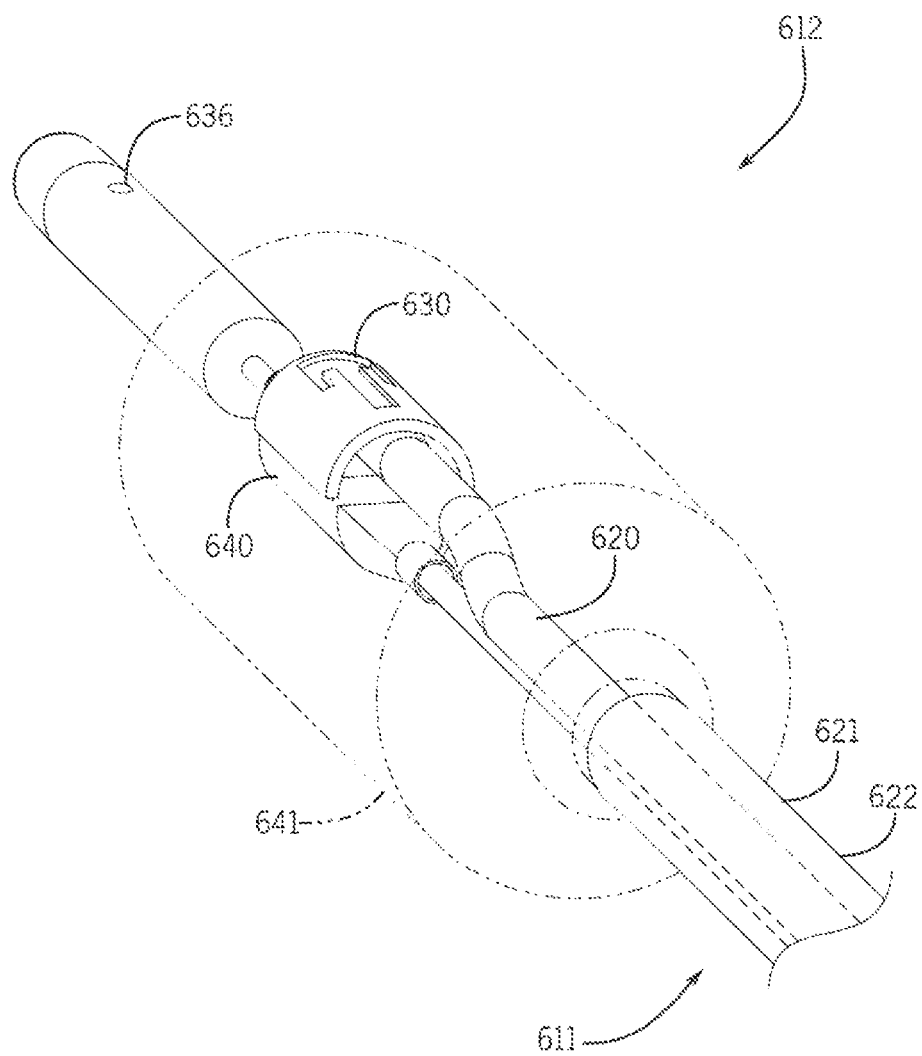
FIG. 37 is a perspective view of an emitter assembly of the device, showing an inner balloon and an outer balloon in phantom.
Figure 38:
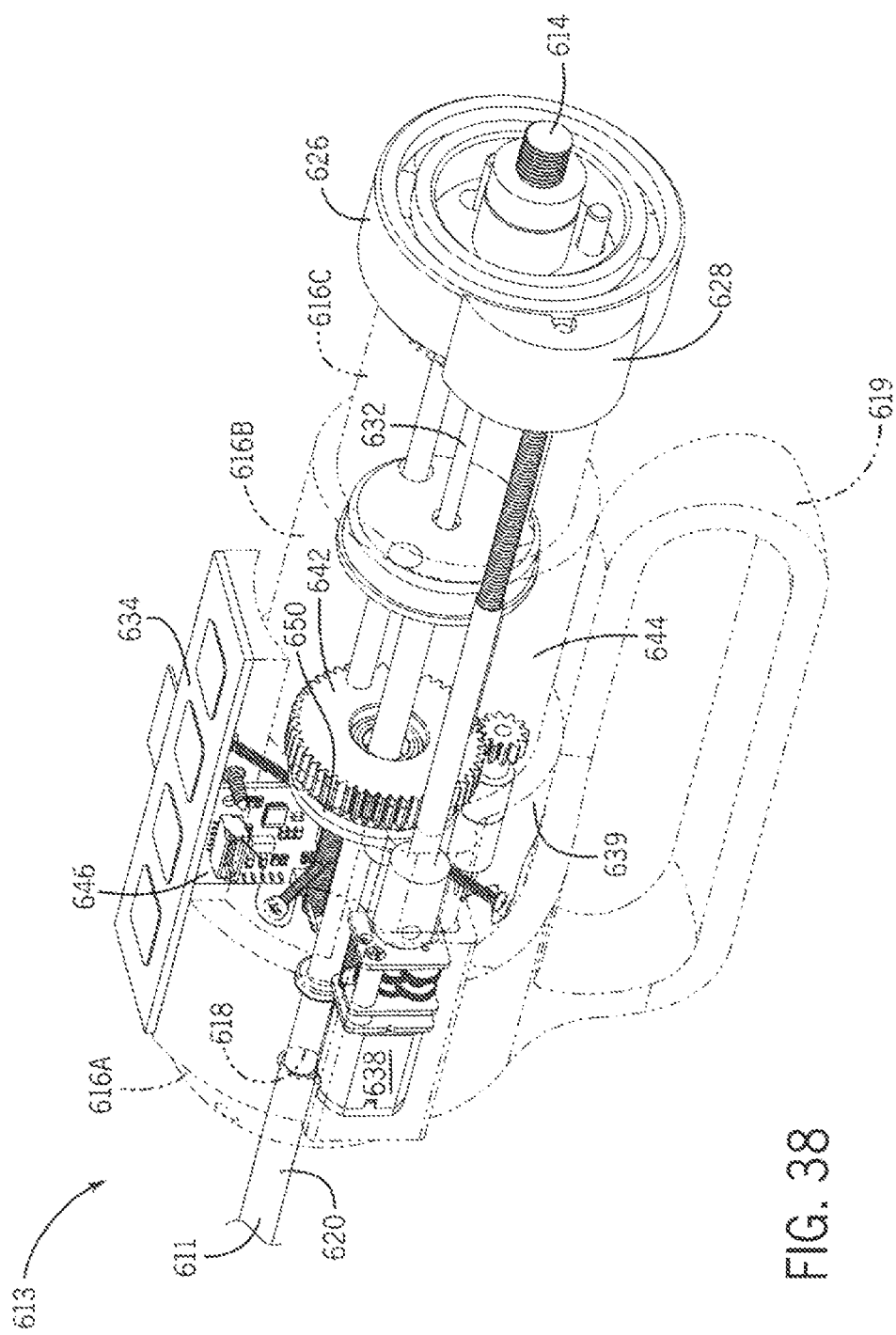
FIG. 38 is a perspective view of the positioner, with housings in phantom.
Figure 39:
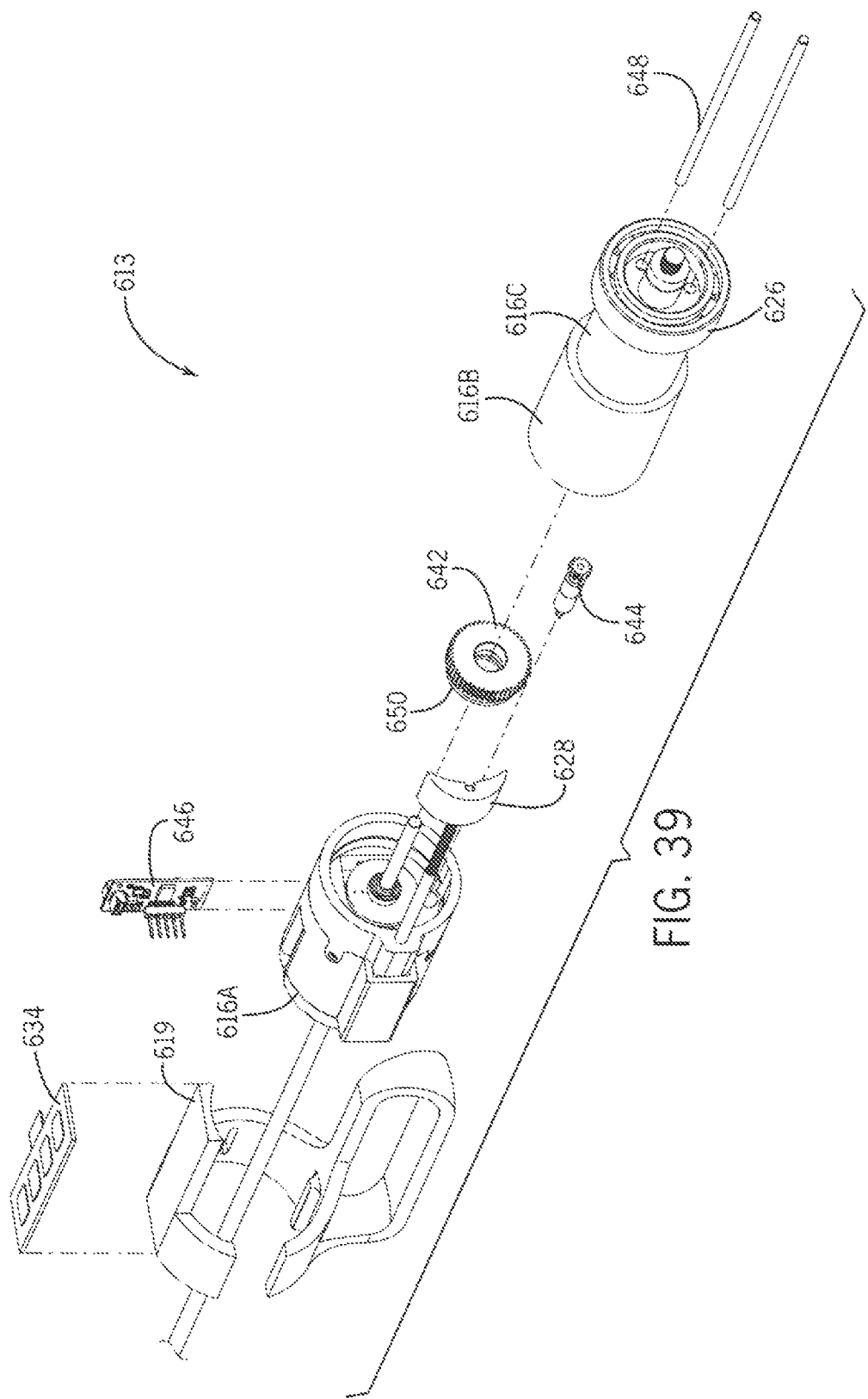
FIG. 39 is an exploded view of the positioner.

Referring to FIG. 37, the antenna assembly includes the antenna 630, the ablation zone indicator 636, the inner balloon 640 and the outer balloon 641. The ablation zone indicator 636 is a visual indicator to show the location of the ablation zone on the target tissue to the physician. This indicator can be an LED, a fiber-optic, or a laser. The location of the indicator 636 can be proximal or distal to the antenna 630, on or under the antenna 630. The indicator 636 can either show the full extents of the ablation zone, the center point of the ablation zone, the boundary of the ablation zone or some combination of the above. The ablation zone indicator 636 receives power from, the slip ring or rotary joint 650 located within the housing 616A. The slip ring or rotary joint 650 allows signal to be transferred between the circuit board 646 and the indicator 636 that is fixed to the inner antenna assembly 612, the assembly 612 being rotatable 360°. In the case that the ablation zone indicator 636 is a fiber optic, a fiber-optic rotary joint would be employed.

Returning to FIGS. 35, 36, 38 and 39, the printed circuit board 646 controls the motors 638, 639 and the activation of the ablation zone indicator 636. It is also communicatively connected to the membrane switch keypad 634 to translate button presses to the appropriate action (motor activation, direction and speed control of the motors and ablation zone indication, on or off). It receives power through a cable (not shown) that is guided through cable housing 648, from an external source, preferably the microwave generator 16.

The embodiments above are chosen, described and illustrated so that persons skilled in the art will be able to understand the invention and the manner and process of making and using it. The descriptions and the accompanying drawings should be interpreted in the illustrative and not the exhaustive or limited sense. The invention is not intended to be limited to the exact forms disclosed. While the application attempts to disclose all of the embodiments of the invention that are reasonably foreseeable, there may be unforeseeable insubstantial modifications that remain as equivalents. It should be understood by persons skilled in the art that there may be other embodiments than those disclosed which fall within the scope of the invention as defined by the claims. Where a claim, if any, is expressed as a means or step for performing a specified function it is intended that such claim be construed to cover the corresponding structure, material, or acts described in the specification and equivalents thereof, including both structural equivalents and equivalent structures, material-based equivalents and equivalent materials, and act-based equivalents and equivalent acts.

The invention claimed is:

1. An ablation system, comprising:
   a catheter having a distal end which is adapted to be inserted into the body of a patient and an opposing proximal end, the catheter having a central lumen and a power cable disposed in the central lumen, the power cable being longitudinally and rotatably movable with respect to the catheter;
   at least one emitter assembly communicatively connected on or near the distal end of the catheter, the emitter assembly being adapted to being inserted into the body of the patient with the catheter, the emitter assembly comprising:
      an outer balloon for establishing a position in the body of the patient
      a microwave antenna disposed within the outer balloon, the microwave antenna being communicatively connected to the power cable, and
      an inner balloon disposed over the microwave antenna and inside the outer balloon for offset positioning the microwave antenna relative to a tissue or tissues of the patient; and
   a handle connected on or near the proximal end of the catheter, the handle being adapted to control insertion of the catheter into the body of the patient and adjusts the longitudinal and rotational positioning of the emitter in the body of the patient, the handle comprising:
      a housing which is separate and distinct from the catheter;
      a rotational motion motor disposed within the housing, the rotational motion motor being connected to the power cable by at least one gear, the rotational motor rotating the power cable whereby the microwave antenna at the distal end of the catheter is rotatable to permit control of direction of ablation; and
      a linear motion motor connected to a distal position on the exterior of the housing, the linear motion motor being connected to a lead screw mechanism which is connected to proximal position on the housing whereby longitudinal position of the microwave antenna and inner balloon is adjustable within the outer balloon.

2. The system of claim 1, wherein the housing is cylindrical and constructed of two overlapping housing members which are movable with respect to each other to facilitate longitudinal movement of the microwave antenna and the inner balloon by the linear motion motor.

3. The system of claim 1, wherein the handle further comprises a keypad communicatively to the rotational motion motor and the linear motion motors for actuating longitudinal and rotational motion of the system, the keypad being disposed on the outside of the housing for access by a user.

4. The system of claim 3, further comprising an electronic controller which is communicatively connected to the keypad and to the motors.

5. The system of claim 1, for human medical therapy.

6. The system of claim 5, for Barrett's Esophagus therapy.

* * * * *